United States Patent [19] [11] 4,061,754
Black [45] Dec. 6, 1977

[54] IMIDAZO[1,2-a]QUINOLINES

[75] Inventor: Robin Michael Black, Porton, England

[73] Assignee: John Wyeth & Brother Limited, Maidenhead, England

[21] Appl. No.: 647,279

[22] Filed: Jan. 7, 1976

[30] Foreign Application Priority Data
Jan. 16, 1975 United Kingdom ............... 1933/75

[51] Int. Cl.$^2$ .................. A61K 31/475; C07D 235/02
[52] U.S. Cl. .............................. 424/258; 260/288 CF; 260/288 R
[58] Field of Search ...... 260/289 C, 288 CE, 288 CF; 424/258

[56] References Cited
PUBLICATIONS
Cookson et al., "J. Chem. Soc., Chem. Comm.", pp. 911 & 912, (1974).
Kwon et al., "Chem. Abstr.", Abstract No. 47935a, vol. 80, (1974).

Primary Examiner—Donald G. Daus
Assistant Examiner—D. B. Springer
Attorney, Agent, or Firm—Arthur E. Wilfond

[57] ABSTRACT

The invention relates to imidazo[1,2-a]quinolines of formula (I)

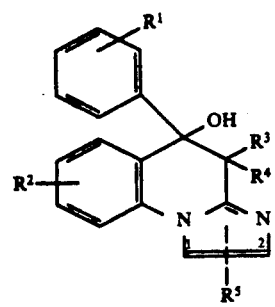

and their pharmaceutically acceptable acid addition salts. In formula I $R^1$ and $R^2$ which may be the same or different each represent hydrogen, lower alkyl, lower alkoxy, trifluoromethyl or halogen, $R^3$ and $R^4$ which may be the same or different each represent lower alkyl and $R^5$ represents hydrogen, lower alkyl, aryl or aryl-loweralkyl. The compounds possess hypotensive activity.

5 Claims, No Drawings

IMIDAZO[1,2-A]QUINOLINES

This invention relates to quinoline derivatives. More particularly, the invention relates to certain novel imidazo[1,2-a]quinolines, to processes for preparing the imidazo[1,2-a]quinolines and to pharmaceutical preparations containing them.

The novel imidazo[1,2-a]quinolines of the present invention are compounds of general formula (I)

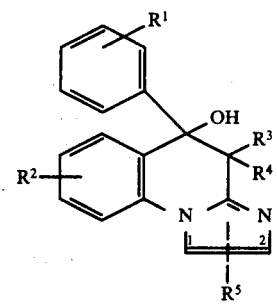

and their pharmaceutically acceptable acid addition salts.

In general formula (I) $R^1$ and $R^2$ which may be the same or different each represent hydrogen, lower alkyl, lower alkoxy, trifluoromethyl or halogen, $R^3$ and $R^4$ which may be the same or different each represent lower alkyl and $R^5$ represents hydrogen, lower alkyl, aryl or arylloweralkyl.

The term "lower" as used herein means that the radical referred to contains 1 to 6 carbon atoms. Preferably the radical contains 1 to 4 carbon atoms.

The following are examples of the groups $R^1$ and $R^2$: hydrogen; lower alkyl (e.g. methyl, ethyl, propyl and butyl); lower alkoxy (e.g. methoxy, ethoxy, propoxy or butoxy); trifluoromethyl and halogen such as fluorine, chlorine and bromine. Preferably both $R^1$ and $R^2$ are hydrogen.

$R^3$ and $R^4$ can be the same or different and they represent lower alkyl radicals (e.g. methyl, ethyl, propyl and butyl). Preferably $R^3$ and $R^4$ are the same and both represent methyl.

$R^5$ can be hydrogen; lower alkyl (e.g. methyl, ethyl, propyl or butyl); aryl (e.g. phenyl optionally substituted by one or more substituents such as those indicated above for the meanings $R^1$ and $R^2$) or aryloweralkyl, (e.g. arylmethyl or arylethyl where "aryl" can be, for example an optionally substituted phenyl radical as mentioned immediately above). Preferably $R^5$ is hydrogen or phenyl.

The compounds of the invention can be prepared by dehydrating the reaction product of an amine of general formula (II)

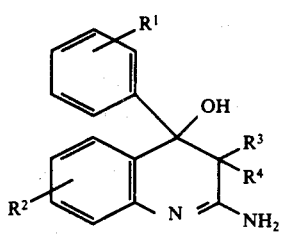

(where $R^1$, $R^2$, $R^3$ and $R^4$ have the meanings given above) and an aldehyde or ketone of general formula (III)

$$R^5CO.CH_2X \qquad (III)$$

(where $R^5$ has the meaning given above and X is a halogen atom or a chemically equivalent replaceable atom or radical, for example, an organic sulphonyl radical such as a tosyl radical). Examples of the compound (III) include phenacyl bromide and chloracetaldehyde. The invention is not limited to any particular structure of the reaction product. The reaction product could, for example, have a cyclic structure such as

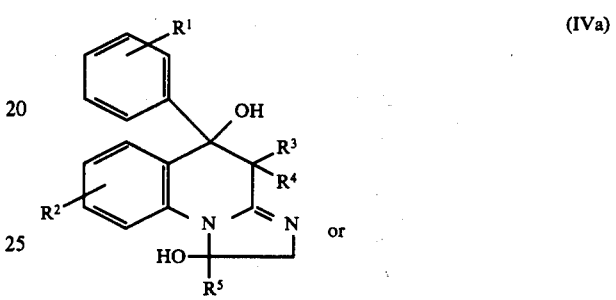

or alternatively the reaction product could be uncyclised, e.g.,

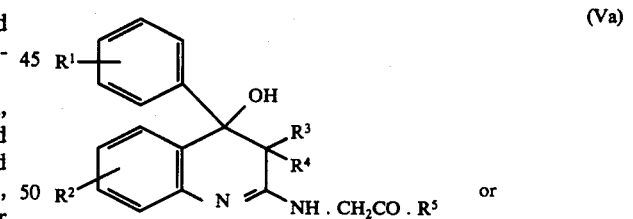

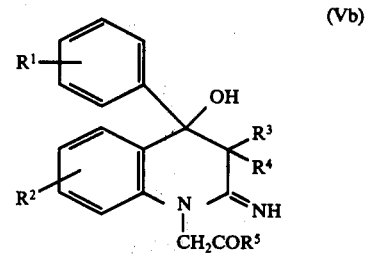

If the reaction product is uncyclised the dehydration process is a cyclodehydration. In order to prepare a compound of the invention an amine of general formula (II) can be reacted with an aldehyde or ketone of general formula (III) and the reaction product dehydrated e.g. by heating in a suitable inert solvent e.g. xylene. It is not necessary to isolate the reaction product before subjecting it to the dehydration process.

The process described above could give a product in which the substituent $R^5$ (if $R^5$ is other than hydrogen) is in either the 1- or 2-position of the imidazo[1,2-a] quinoline nucleus. It is believed that the product has the substituent $R^5$ in the 1- position but the general formula (I) is used herein to define the products formed by the above process whether the R group is in the 1-or 2- position.

The amines of general formula (II) may be prepared by reacting an aminobenzophenone of general formula (VI)

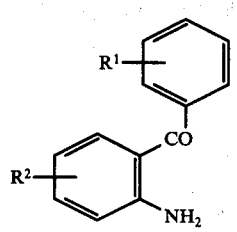
(VI)

with a nitrile of general formula (VIII)

(VIII)

This process is described in my co-pending concurrently filed application Ser. No. 647,278 entitled Certain 2-Substituted 4-Phenylquinoline-4-Ols (corresponding to U.K. Application No. 1932/75).

Examples of acid addition salts are those formed from inorganic and organic acids such as sulphuric, hydrochloric, hydrobromic, phosphoric, tartaric, fumaric, maleic, citric, acetic, formic, methanesulphonic and p-toluenesulphonic acids.

The compounds of the invention possess at least one asymmetric carbon atom and hence optical enentiomorphs are possible. The compounds of the invention may be in the form of optical isomers or mixtures of isomers, e.g. racemates. The optical isomers may be prepared from racemic mixtures by the use of standard methods described in the literature. They may also be prepared by employing optical active enantiomers of formula (II) as starting materials.

The compounds of the invention possess hypotensive activity as indicated by a standard pharmacological procedure. In such a procedure the compounds are administered intravenously to normotensive anaesthetised rats and the fall in diastolic blood pressure is measured 15 minutes after administration. Generally, the compounds produce a 30 mm Hg or more fall in blood pressure in this test when administered at a dosage of at least 25.6 mg/kg. Some of the compounds are active at lower dosages. For example, 4,5-dihydro-4,4-dimethyl-5-phenylimidazo [1,2-a]quinolin-5-ol shows sustained hypotension in the above procedure at a dosage level of 6.5 mg/kg.

The invention further provides a pharmaceutical composition which comprises a compound of formula (I) or a pharmaceutically acceptable acid addition thereof, in association with a pharmaceutically acceptable carrier. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredients. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture or both. Preferably a liquid carrier is one suitable for parenteral injection. Where the active ingredient is sufficiently soluble it can be dissolved in normal saline as a carrier; it it is too insoluble for this it can be dissolved in a suitable organic solvent, for instance aqueous propylene glycol containing from 10 to 75% of the glycol by weight is generally suitable.

In other instances compositions can be made by dispersing the finely-dividing active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule or tablet itself, or it can be the appropriate number of any of these in packaged form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form. The daily dose of compound will vary depending upon the route of administration, the particular compound employed and the particular animal involved. The daily dose could be, for example, within the range 0.5 to 25 mg/kg depending upon the method of administration and the specific compound.

The following Examples illustrate the invention:

EXAMPLE 1

4,5-Dihydro-4,4-dimethyl-1,5 or 2,5-diphenylimidazo [1,2-a]quinolin-5-ol

To a solution of 2-amino-3,4-dihydro-3,3-dimethyl-4-phenylquinolin-4-ol(10.64 g., 0.02 mole) in dry dioxan (75 ml) was added phenacyl bromide (4.0 g., 0.062 mole). The mixture was stirred for 28 hours, after which the precipitate of the hydrobromide of 2-amino-3,4-dihydro-3,3-dimethyl-4-phenylquinolin-4-ol was removed by filtration, the dioxan was evaporated and the residue triturated with toluene to give an uncyclised intermediate (3.402 g., m.p. 165°-170° C). A solution of the intermediate in dried xylene (200 ml) was refluxed under a Dean and Stark head for 8 hours, cooled, the xylene evaporated to give a residue which was converted to its hydrochloride in isopropyl alcohol. The product was recrystallised from absolute ethanol to give the title compound as its hydrochloride (1.28 g., m.p. 198°-200° C).

[Found: C, 73.2; H, 5.8; N, 6.8%. $C_{25}H_{22}N_2O.HCl \cdot \frac{1}{2}H_2O$ requires C, 72.9; H, 5.9; N, 6.8%].

EXAMPLE 2

4,5-Dihydro-4,4-dimethyl-5-phenylimidazo[1,2-a]quinolin-5-ol

To a solution of freshly prepared chloroacetaldehyde (2.30 g., 0.03 mole) in absolute ethanol (50 ml.) and water (12.5 ml.) was added a solution of 2-amino-3,4-dihydro-3,3-dimethyl-4-phenylquinolin-4-ol (6.66 g., 0.025 mole) in absolute alcohol (62.5 ml). Sodium bicarbonate (2.5 g) was added and the mixture refluxed for 6 hours. After cooling, a small precipitate was filtered off, and the filtrate concentrated in vacuo, taken up in water, extracted with ether, dried and evaporated. The residue was crystallised from isopropyl alcohol to give an intermediate (3.77 g., m.p. 188°-190° C). A solution of this intermediate in dried xylene (200 ml.) was refluxed under a Dean and Stark head for 21 hours, cooled and the xylene evaporated. The hydrochloride of the residue was recrystallised from isopropyl alcohol to give the title compound as its hydrochloride (2.4 g., 258°-260° C).

[Found: C, 68.8; H, 6.1; N, 8.3% $C_{19}H_{18}N_2OHCl.1/4H_2O$ requires C, 68.9; H, 5.9; N, 8.5%].

EXAMPLE 3

By procedures analogous to that of Example 2 chloracetaldehyde is reacted with
a. 2-amino-3,4-dihydro-3,3-dimethyl-6-methoxy-4-phenylquinolin-4-ol,
b. 2-amino-3,4-dihydro-3,3,6-trimethyl-4-phenylquinolin-4-ol,
c. 2-amino-6-chloro-3,4-dihydro-3,3-dimethyl-4-phenylquinolin-4-ol,
d. 2-amino-6-chloro-4-(o-chlorophenyl)-3,4-dihydro-3,3-dimethylquinolin-4-ol,
and
e. 2-amino-3,4-dihydro-3,3-dimethyl-4-phenyl-6-trifluoromethylquinolin-4-ol
to give, respectively:
a. 4,5-dihydro-4,4-dimethyl-7-methoxy-5-phenylimidazo[1,2-a]quinolin-5-ol,
b. 4,5-dihydro-4,4-dimethyl-7-methyl-5-phenylimidazo[1,2-a]quinolin-5-ol,
c. 7-chloro-4,5-dihydro-4,4-dimethyl-5-phenylimidazo[1,2-a]quinolin-5-ol,
d. 7-chloro-5-(o-chlorophenyl)-4,5-dihydro-4,4-dimethylimidazo[1,2-a]quinolin-5-ol
and
e. 4,5-dihydro-4,4-dimethyl-5-phenyl-7-trifluoromethylimidazo[1,2-a]quinolin-5-ol.

EXAMPLE 4

2-Amino-3,4-dihydro-3,3-dimethyl-4-phenylquinolin-4-ol is reacted with
a. p-chlorophenacyl bromide
and
b. p-methylphenacyl bromide
by procedures analogous to that of Example 1 to give, respectively,
a. 1 or 2-(p-chlorophenyl)-4,5-dihydro-4,4-dimethyl-5-phenylimidazo[1,2-a]quinolin-5-ol
and
b. 4,5-dihydro-4,4-dimethyl-1 or 2-(p-methylphenyl)-5-phenylimidazo[1,2-a]quinolin-5-ol.

EXAMPLE 5

1,4,4 or 2,4,4-Trimethyl-5-phenyl-4,5-dihydroimidazo[1,2-a]quinolin-5-ol.

Following the method of example 2, chloroacetone (0.03mole) in a mixture of water and alcohol is reacted with 2-amino-3,4-dihydro-3,3-dimethyl-4-quinolin-4-ol (0.025 mole) and sodium bicarbonate (2.5g). After the intermediate has been obtained it is heated under reflux with a Dean and Stark head in xylene (100-200ml) until water ceases. to be collected or the reaction is shown to be complete by t.l.c. After removal of the xylene the product is obtained in the usual fashion as its hydrochloride salt.

EXAMPLE 6

Following the procedure of Example 1,2-amino-3,4-dihydro-3,3-dimethyl-4-phenylquinolin-4-ol is reacted with 1-chloro-3-phenylpropan-2-one, 1-chloro-3-(p-chlorophenyl)propan-2-one, 1-chloro-3-(p-methyl)propan-2-one and 1-chloro-3-(p-methoxyphenyl)propan-2-one (see Brewster et al Synthesis, 1971,307-308) to give respectively
a. 1 or 2-benzyl-4,5-dihydro-4,4-dimethyl-5-phenylimidazo[1,2-a]quinolin-5-ol
b. 1 or 2-(p-chlorobenzyl)-4,5-dihydro-4,4-dimethyl-5-phenylimidazo[1,2-a]quinolin-5-ol
c. 1 or 2-(p-methylbenzyl)-4,5-dihydro-4,4-dimethyl-4-phenylimidazo[1,2-a]quinolin-5-ol
and
d. 1 or 2-(p-methoxybenzyl)-4,5-dihydro-4,4-dimethyl-5-phenylimidazo[1,2-a]quinolin-5-ol.

I claim:

1. An imidazo[1,2-a]quinoline selected from the group consisting of compounds having the formula (I)

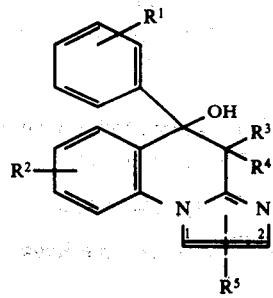

and the pharmaceutically acceptable acid addition salts thereof, wherein $R^1$ and $R^2$ which may be the same or different each represent hydrogen, lower alkyl, lower alkoxy, trifluoromethyl or halogen, $R^3$ and $R^4$ which may be the same or different each represent lower alkyl and $R^5$ represents hydrogen, lower alkyl, phenyl, phenyl substituted by $R^1$ or phenylloweralkyl, with the proviso that $R^3$ and $R^4$ cannot be groups which give rise to steric hindrance.

2. An imidazo[1,2-a]quinoline according to claim 1 wherein $R^5$ is hydrogen or phenyl.

3. A compound according to claim 1 which is 4,5-dihydro-4,4-dimethyl-1,5 or 2,5-diphenylimidazo [1,2-a]quinolin-5-ol or a pharmaceutically acceptable acid addition salt thereof.

4. A compound according to claim 1 which is 4,5-dihydro-4,4-dimethyl-5-phenylimidazo[1,2-a]quinolin-5-ol or a pharmaceutically acceptable acid addition salt thereof.

5. A hypotensive composition comprising a hypotensively effective amount of an imidazol[1,2-a]quinoline selected from the group consisting of compounds having the formula (I) and the pharmaceutically acceptable acid addition salts thereof, wherein $R^1$ and $R^2$ which may be the same or different each represent hydrogen, lower alkyl, lower alkoxy, trifluoromethyl or halogen, $R^3$ and $R^4$ which may be the same or differnt each represent lower alkyl and $R^5$ represents hydrogen, lower alkyl, phenyl, phenyl substituted by $R^1$ or phenyllower-alkyl, with the proviso that $R^3$ and $R^4$ cannot be groups which give rise to steric hindrance in association with a pharmaceutically acceptable carrier.

* * * * *